United States Patent
Relkin

(10) Patent No.: US 8,722,042 B2
(45) Date of Patent: *May 13, 2014

(54) USE OF VENTRICULAR ENLARGEMENT RATE IN INTRAVENOUS IMMUNOGLOBULIN TREATMENT OF ALZHEIMER'S DISEASE

(75) Inventor: Norman R Relkin, Harrington Park, NJ (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,886

(22) Filed: Oct. 17, 2011

(65) Prior Publication Data
US 2012/0071747 A1   Mar. 22, 2012

Related U.S. Application Data

(63) Continuation of application No. 13/086,285, filed on Apr. 13, 2011, now Pat. No. 8,066,993.

(60) Provisional application No. 61/323,739, filed on Apr. 13, 2010.

(51) Int. Cl.
*C07K 16/06* (2006.01)
*A61K 39/00* (2006.01)
*A61P 25/28* (2006.01)

(52) U.S. Cl.
USPC ............ 424/130.1; 424/142.1; 514/17.8; 530/387.1

(58) Field of Classification Search
None
See application file for complete search history.

(56) References Cited

U.S. PATENT DOCUMENTS

2009/0155256 A1   6/2009   Black et al.

FOREIGN PATENT DOCUMENTS

WO   WO 2009/017467   2/2009

OTHER PUBLICATIONS

Salloway et al., Neurology, 77:1253-1262, 2011.*
Brinkman et al., Am J Psychiatry., 114(1):81-83, 1984.*
Schott et al., Neurology, 65:119-124, Jul. 2005.*
Fox et al., "Effects of Aβ immunization (AN1792) on MRI measures of cerebral volume in Alzheimer disease," 2005, Neurology, 64, pp. 1563-1572.
Gilman et al., "Clinical effects of Aβ immunization (AN1792) in patients with AD in an interrupted trial," 2005, Neurology, 64, 1553-1562.
Jack et al. "MRI as a Biomaker of Disease Progression in a Therapeutic Trial of Milameline for AD," 2003, Neurology, 60(2); pp. 253-260.
Krishman et al., "Randomized, Placebo-Controlled Trial of the Effects of Donepezil and Neuronal Markers and Hippocampal Volumes in Alzheimer's Disease," 2003, Am. J. Psychiatry, 160: 11: pp. 2003-2011.
Mueller et al., "Evaluation of treatment effects in Alzheimer's and other neurodegenerative diseases by MRI and MRS," 2006, NMR Biomed., 16(6), pp. 655-668.
Ridha et al., "Volumetric MRI and cognitive measures in Alzheimer's disease," 2008, J. Neurol. 255: 567-574.
Tsakanikas et al., "Effects of uninterrupted intravenous immunoglobulin treatment of Alzheimer's disease for 9 months," 2008, presented at the Alzheimer's Association International Conference on Alzheimer's Disease (ICAD), Chicago, IL, ICAD-2008; Abstract 08-A3147.
Dodel et al, Drugs, 70(5):513-528, Mar. 26, 2010.
Salloway et al., Neurology 73:2061-2070, 2009.
International Search Report and Written Opinion dated Jun. 24, 2011, issued in related International Application No. PCT/US2011/032232, filed Apr. 13, 2011.
Nestor et al., "Ventricular enlargement as a possible measure of Alzheimer's disease progression validated using the Alzheimer's disease neuroimaging initiative database," 2008, Brain, 131, pp. 2443-254.
Evans et al., "IVIG Reduced Brain Atrophy in Alzheimer's," Clinical Psychiatry News [online], Jun. 2010 [retrieved on Jun. 10, 2010]. Retrieved from the Internet: <URL : http://psych.imng.com/fileadmin/content_pdf/cpn/archive_pdf/vol38iss6/70262_main.pdf].

* cited by examiner

*Primary Examiner* — Daniel E Kolker
*Assistant Examiner* — Stacey N MacFarlane
(74) *Attorney, Agent, or Firm* — Kilpatrick Townsend & Stockton LLP

(57) ABSTRACT

The present invention relates to the use of MRI monitoring of ventricular enlargement rate as an objective measure for the purpose of assessing disease progression in patients suffering from Alzheimer's disease and for the purpose of determining therapeutic effectiveness of a treatment regimen for Alzheimer's patients. Methods for treating Alzheimer's Disease and monitoring therapeutic effectiveness are provided.

9 Claims, 21 Drawing Sheets

Mean Change in ADAS-Cog Score from Baseline to 18 Months

USE OF VENTRICULAR ENLARGEMENT RATE IN INTRAVENOUS IMMUNOGLOBULIN TREATMENT OF ALZHEIMER'S DISEASE

RELATED APPLICATIONS

This application is a continuation of U.S. patent application Ser. No. 13/086,285, filed Apr. 13, 2011, which claims priority to U.S. Provisional Patent Application Ser. No. 61/323,739, filed Apr. 13, 2010, the contents of each of the above are incorporated by reference in the entirety.

BACKGROUND OF THE INVENTION

Alzheimer's disease is the most common form of dementia afflicting as many as 5.3 million Americans. The disease is generally believed to be caused by the accumulation of β-amyloid plaques in the brain, resulting in nerve cell death and concomitant reduction in neurotransmitters levels. Impairment in memory, cognition, reasoning, and judgment results along with the decrease in emotional stability and development of behavioral problems. The disease is progressive leading to profound mental deterioration and ultimately death.

There is no known cure for the Alzheimer's disease. Patient care primarily focuses on the management of symptoms of this disease. Disease progression in Alzheimer's patients can be monitored in terms of reduction in brain tissue volume, or enlargement of ventricular volume, over time. Afforded by technologies such as magnetic resonance imaging (MRI), these image-based monitoring techniques are advantageous in their ease to administer and to quantify any changes in the brain condition. The recent discovery that antibodies against β-amyloid are present in human immunoglobulin preparations (e.g., intravenous immunoglobulin or IVIG) and can inhibit the neurotoxic effects of β-amyloid lead to clinical trials in Alzheimer's patients. Disease stabilization and modest improvement in cognitive ability were noted.

In 2006, there were 26.6 million Alzheimer's disease sufferers worldwide. By 2050, a predicted 1 in every 85 people will be diagnosed globally. Given the dire nature of this disease, the large patient population, and the tremendous burden on care givers, a pressing need exists for new and more effective therapeutic agents and methods. The present invention provides improvements to fulfill this and other related needs.

BRIEF SUMMARY OF THE INVENTION

This inventions relates to the use of change in ventricular volume to monitor the effect of a brain preserving treatment of Alzheimer's disease and guide formulating further treatment plans. In one aspect, the invention provides a method for treating Alzheimer's disease in a subject in need thereof. The method is useful to determine whether a particular treatment dose and/or frequency is effective after a time period of treatment, the determination is then used to guide modification of future treatment. Typically, if a determination of effectiveness is made, the same dose and/or frequency is maintained; if a determination of ineffectiveness is made, a higher dose and/or frequency is used for a subsequent time period before the effectiveness is assessed again. Specifically, the method includes these sequential steps: (a) determining ventricular volume in the subject's brain by magnetic resonance imaging (MRI), thereby obtaining a baseline value of ventricular volume; (b) administering a brain preserving therapeutic agent to the subject for the purpose of treating Alzheimer's disease during a first time period; (c) determining ventricular volume in the subject's brain by MRI, thereby obtaining a first intermediate value of ventricular volume; (d) comparing the intermediate value from step (c) with the baseline value from step (a); and (e) increasing administration of the brain preserving therapeutic agent in dose or frequency when step (d) indicates an increase from the baseline value to the first intermediate value and the increase is equal to or greater than an expected increase in ventricular volume in a subject with Alzheimer's disease but without receiving treatment for the disease within a time period of the same duration as the first time period, or, maintaining administration of the brain preserving therapeutic agent in dose or frequency when step (d) indicates no increase from the baseline value to the first intermediate value or indicates an increase that is less than an expected increase in ventricular volume in a subject with Alzheimer's disease but without receiving treatment for the disease within a time period of the same duration as the first time period.

In some embodiments, steps (b) to (d) are further repeated at least once, and in each repeat the latest intermediate value is compared with the second latest intermediate value to determine future administration of the therapeutic agent in the same manner as step (e).

In some cases, a determination of ineffectiveness will be made after at least round of repeat treatment at an increased dose and/or frequency schedule (e.g., when steps (b) to (d) have already been repeated at least once) and treatment will then be discontinued. This is often seen when the latest dose and/or frequency is already relatively high within the commonly used dose and/or frequency range. As such, when step (d) of the claimed method during any repeat indicates an increase from one intermediate value to its subsequent intermediate value and the increase is equal to or greater than an expected increase in ventricular volume in a subject with Alzheimer's disease but without receiving treatment for the disease within a time period of the same duration as the time period between the two intermediate values, and the administration of the brain preserving therapeutic agent is increased in dose or frequency, the method further comprises these steps: (f) determining ventricular volume in the subject's brain by MRI after an additional time period during which the therapeutic agent is administered to the subject, thereby obtaining additional intermediate value of ventricular volume; (g) comparing the additional intermediate value with its previous intermediate value; and (h) discontinuing further administration of the therapeutic agent when step (g) indicates an increase from the previous intermediate value to the additional intermediate value and the increase is equal to or greater than an expected increase in ventricular volume in a subject with Alzheimer's disease but without receiving brain preserving treatment for the disease within a time period of the same duration as the additional time period, or, maintaining administration of the brain preserving therapeutic agent in dose or frequency when step (g) indicates no increase from the previous intermediate value to the additional intermediate value or indicates an increase that is less than an expected increase in ventricular volume in a subject with Alzheimer's disease but without receiving treatment for the disease within a time period of the same duration as the additional time period.

In some embodiments, the time interval, e.g., the first, second, or any subsequent time period, may be 3 months, 6 months, 9 months, 12 months, or 18 months. In some embodiments, the therapeutic agent is an immunoglobulin-based brain preserving therapeutic agent, such as an immunoglobulin G. In particular embodiment, the therapeutic agent is IVIG, frequently administered intravenously. In some cases, the IVIG is administered at about 0.2 to 2 grams per kg body weight of the subject. The frequency of administration may be once a week, twice a week, once a month, or twice a month. In one example, the IVIG is administered at about 0.4 gram per kg body weight of the subject twice a month.

In another aspect, the invention provides a method for assessing the efficacy of a brain preserving therapy intended for treating Alzheimer's disease. The method includes these steps: (a) determining the rate of change in ventricular volume of subjects suffering from Alzheimer's disease but not receiving the therapy, thereby obtaining an average rate of change in ventricular volume as a non-therapeutic rate of ventricular volume change; (b) determining the rate of change in ventricular volume of subjects suffering from Alzheimer's disease and receiving the therapy, thereby obtaining an average rate of change in ventricular volume as a therapeutic rate of ventricular volume change; and (c) comparing the therapeutic rate with the non-therapeutic rate, thereby determining the efficacy of the therapy. The ventricular volume in steps (a) and (b) is determined by magnetic resonance imaging (MRI). The therapy is deemed effective when the therapeutic rate is lower than the non-therapeutic rate, and the therapy is deemed ineffective when the therapeutic rate is equal to or greater than the non-therapeutic rate.

In some embodiments, the rate of change in ventricular volume in step (a) or (b) is determined over a time period of about 3 months, 6 months, 9 months, 12 months, or 18 months.

In some embodiments, the therapy is by administration of an immunoglobulin-based brain preserving therapeutic agent, such as an immunoglobulin G. In one example, the therapy is IVIG administration, preferably intravenously. For example, the IVIG may be administered at about 0.2 to 2 grams per kg body weight of the subject per month. The frequency of administration may be once a week, twice a week, once a month, or twice a month. In one exemplary treatment plan, the IVIG is administered at about 0.4 gram per kg body weight of the subject twice a month.

DEFINITIONS

Figure 1:
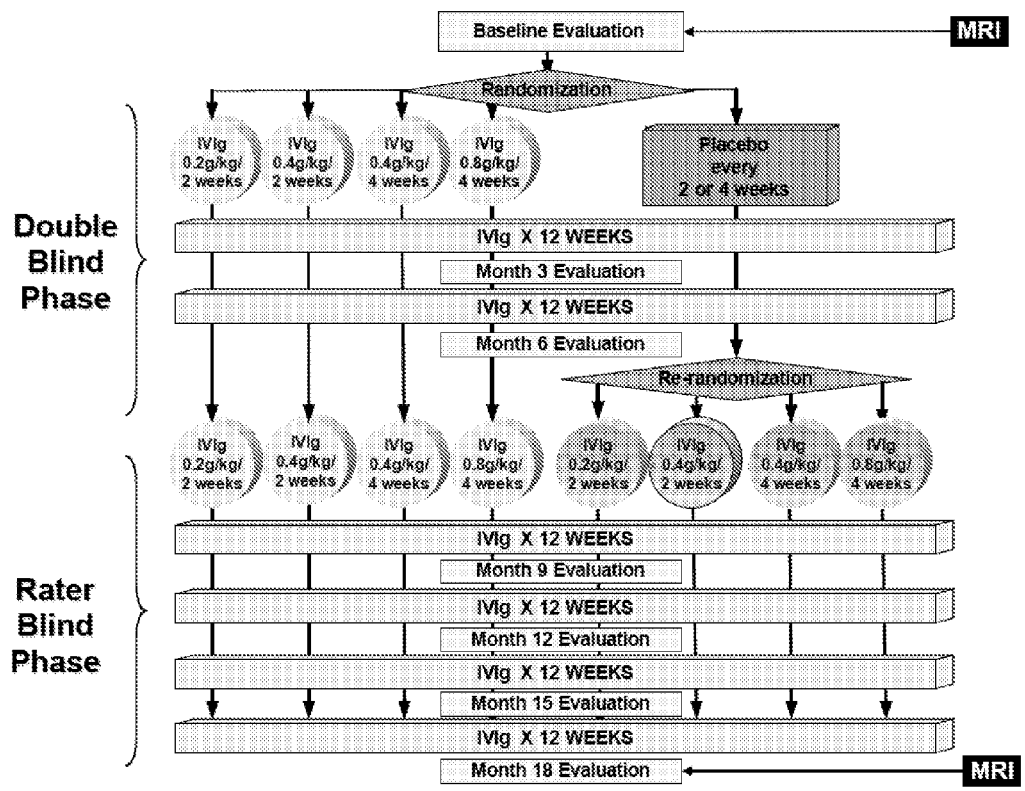
FIG. 1 is a schematic presentation of the 18-month IVIG study design.

"Alzheimer's disease (AD)" is a common form of dementia typically observed among people over 65 years of age, although the early-onset type may occur much earlier. An incurable, irreversible, progressive brain disease, Alzheimer's disease is diagnosed based on certain common symptoms. In the early stages, the most commonly recognized symptom of AD is memory loss, such as difficulty in remembering recently learned facts. A physician will typically confirm the diagnosis of AD with behavioral assessments and cognitive tests, often followed by a brain scan. As the disease advances, further symptoms will become evident, including confusion, irritability and aggression, mood swings, language breakdown, long-term memory loss, and the general withdrawal of the patients as their senses decline. As used herein, a patient suffering from Alzheimer's disease or AD may be afflicted with any variation of the brain disorder and at any stage of the condition as diagnosed according to the currently used diagnostic criteria.

The ventricular system is a set of structures containing cerebrospinal fluid in the brain. It includes four interconnected ventricles and is continuous with the central canal of the spinal cord. As used herein, the term "ventricular volume" or "ventricular space" refers to the entire space of ventricular system within which the cerebrospinal fluid is contained. Ventricular space can be visualized by imaging techniques such as CT scan and magnetic resonance imaging (MRI), and can be quantitatively measured with the aid of various computer software. A number of conditions are known to exhibit ventricular space enlargement, often a continuous process as the conditions progress. The term "ventricular enlargement rate" refers to the increase of ventricular volume over a specified amount of time (for example, per year) as indicated by changes quantified through imaging techniques such as CT scan or MRI.

As used herein, an "immunoglobulin-based brain preserving therapeutic agent" refers to any therapeutic composition that comprises one or more immunoglobulins and is used for treating patients suffering from a condition that involves accelerated brain shrinkage (e.g., Alzheimer's disease) for preventing, reducing, or reversing such accelerated shrinkage. For example, such a composition may comprise one or more immunoglobulin (e.g., immunoglobulin G), which may be naturally occurring, recombinantly produced, or a portion of an immunoglobulin (especially a binding portion thereof, e.g., a Fab or $F(ab')_2$ fragment, or a single chain antibody). Examples of such an antibody-based brain preserving therapeutic agent can be found in, e.g., US2009/0155256.

"Intravenous immunoglobulin" or "IVIG" refers to a blood product that contains the pooled immunoglobulin G (IgG) immunoglobulins from the plasma of a large number (often more than a thousand) of blood donors. Typically containing more than 95% unmodified IgG, which has intact Fc-dependent effector functions, and only trace amounts of immunoglobulin A (IgA) or immunoglobulin M (IgM), IVIGs are sterile, purified IgG products used in treating certain medical conditions. Although the term "intravenous" indicates administration by intravenous injection, as this term is used in this patent application, IVIG compositions also encompass IgG compositions that are formulated for and administered by different routes, including subcutaneous administration.

When used in the context of describing a treatment method of Alzheimer's disease where the ventricular volume of a therapy recipient is monitored for the purpose of determining whether the therapeutic regimen should be adjusted for a subsequent time period, "an expected increase in ventricular volume in a subject with Alzheimer's disease but without receiving brain preserving therapy for the disease" refers to the amount of ventricular enlargement that would be anticipated in an Alzheimer patient not receiving anti-Alzheimer brain preserving treatment during the same length of time. This amount of ventricular enlargement is due to natural progression of the disease at an average pace. In practice, this amount is the average amount calculated from a group of untreated individuals, who have Alzheimer's disease but have received no treatment for preservation of brain volume and function, or have received only symptom-alleviating treatment that does not preserve brain volume (e.g., anti-cholinesterase or ACEI and memantidine treatment), for the disease, when observed under conditions otherwise comparable to those Alzheimer patients who have received brain preserving treatment (or treated individuals). Preferably, the IVIG-treated and IVIG-untreated individuals should be reasonably matched in terms of being at similar stages or severity of Alzheimer's disease, as well as in other aspects such as duration of disease, age, gender, medical history, ethnic background, level of education. The changes in ventricular volume between the treated and untreated individuals should be compared after it is taken into consideration the length of time during which such changes take place. For instance, the expected annual ventricular enlargement for an average untreated Alzheimer's disease patient is determined to be about 10%, even though the actual time period for making the observation and calculation can be longer or shorter than one year. In addition, the untreated group used to calculate an expected rate of ventricular enlargement or brain atrophy is preferred to be of a reasonable size, for example, including at least 5 or 10 or more individuals. Average rates for ventricular volume increase and brain atrophy for untreated individuals with Alzheimer's disease have been determined and are well known by those of skill in the art (see, e.g., Frisoni et al., 2010, *Neurology* 6:67-77).

DETAILED DESCRIPTION OF THE INVENTION

I. Introduction

Ventricular enlargement occurs as a consequence of brain atrophy in Alzheimer's Disease (AD) and correlates with cognitive decline and increasing Alzheimer neuropathology. Utilizing serial magnetic resonance imaging (MRI) to monitor the ventricular enlargement rate (VER) among individuals who suffer from mild to moderate AD, the present inventors used VER as an objective means to assess the effects of intravenous immunoglobulin (IVIG) immunotherapy. IVIG treatment has been shown to achieve significantly reduced rates of ventricular enlargement. This effect has been observed as varying with IVIG dosage and correlating with reduced cognitive decline in the patients. These results indicate that IVIG therapy can significantly reduce the rate of brain atrophy, a hallmark of neurodegeneration and therefore disease progression in AD patients. Although various cognitive tests are available for assessing a patient's brain function, the use of imaging techniques such MRI for quantitatively monitoring VER provides a quick and objective means for monitoring any changes in AD patients' cognitive ability in response to a brain preserving therapy. Imaging techniques also allow direct measurement of whole brain volume to indicate brain atrophy in AD patients and therefore indicate therapeutic efficacy of a brain preserving agent in treating AD. The present inventors have observed statistically significant changes in whole brain volume (reduction of whole brain shrinkage rate) among AD patients receiving brain preserving treatment after some time period, e.g., 12 months. VER monitoring in comparison with whole brain measurement is more sensitive and can provides an indication of brain volume change in a relatively shorter time period, such as within 3 months or 6 months, following the start of a brain preserving treatment. The VER method is therefore relatively faster for detecting changes in AD patient brain volume and efficacy of a brain preserving therapy.

II. IVIG Treatment of Alzheimer's Disease

A. Patients to Receive Treatment

Patients to receive the IVIG treatment (or other anti-Alzheimer brain preserving therapeutic agents) according to the present invention are diagnosed to suffer from Alzheimer's disease. The onset of Alzheimer's disease is usually gradual, and it is slowly progressive. Problems with memory, particularly short-term memory, are common early in the course of Alzheimer's disease. Mild personality changes, such as less spontaneity, apathy, and a tendency to withdraw from social interactions, may also occur early in the illness. As the disease progresses, problems in abstract thinking and in other intellectual functions develop. The patient may begin to have trouble with figures when working on bills, with understanding what is being read, or with organizing the day's work. Further disturbances in behavior and appearance may also be seen at this point, such as agitation, irritability, quarrelsomeness, and a diminishing ability to dress appropriately. Later in the course of the disorder, affected individuals may become confused or disoriented about what month or year it is, be unable to describe accurately where they live, or be unable to name a place being visited. Eventually, patients may wander, become unable to engage in conversation, erratic in mood, uncooperative, and lose bladder and bowel control. In late stages of the disease, persons may become totally incapable of caring for themselves. Death can then follow, perhaps from pneumonia or some other problem that occurs in severely deteriorated states of health. Those who develop the disorder later in life more often die from other illnesses (such as heart disease) rather than as a consequence of Alzheimer's disease.

The clinical criteria for diagnosing Alzheimer's disease are well known to a practicing physician. Alzheimer's disease is diagnosed when: (1) a person has sufficient cognitive decline to meet criteria for dementia; (2) the clinical course is consistent with that of Alzheimer's disease; and (3) no other brain diseases or other processes are better explanations for the dementia. Other causes for the cognitive problems must be ruled out before a diagnosis of Alzheimer's disease can be properly made. They include neurological disorders such as Parkinson's disease, cerebrovascular disease and strokes, brain tumors, blood clots, and multiple sclerosis, infectious diseases of the central nervous system, side effects of medications, psychiatric disorders, substance abuse, metabolic disorders, trauma, toxic factors, etc. In short, a comprehensive clinical evaluation is essential in arriving at the correct diagnosis. Such an evaluation should include at least three major components; (1) a thorough general medical workup; (2) a neurological examination including testing of memory and other functions of thinking; and (3) a psychiatric evaluation to assess mood, anxiety, and clarity of thought. In addition, imaging of the brain is sometimes used for evaluation purposes. Frequently used techniques for imaging include non-contrast CT scan and MRI. Other imaging procedures (such as SPECT, PET, and fMRI) can provide information of brain function (functional neuroimaging) but are less often used.

For the purpose of practicing the method of this invention, Alzheimer patients receiving anti-Alzheimer treatment (e.g., IVIG administration) are typically in the relatively early stages of the disease progression with mild to moderate symptoms, such that their improvement from the therapeutic agent will be easier to determine and thus their future treatment plan can be properly adjusted. In the some cases, individuals suspected of beginning to develop Alzheimer's disease or considered at risk of developing this disease may also receive such treatment, so that their progression towards onset of the disease may be halted or reversed, or their risk of developing the disease may be diminished or eliminated. In other words, the anti-Alzheimer treatment (e.g., IVIG administration) can be applied as a method of preventing Alzheimer's disease or inhibiting or delaying the onset of the disease in at-risk individuals with no or only suspected symptoms.

In some cases a therapeutic agent intended for treating Alzheimer's disease is assessed for its efficacy, in which cases Alzheimer's patients are placed in treatment and non-treatment groups for comparison purposes, for example, to demonstrate any change in ventricular enlargement rate attributable to the effects of the therapeutic agent. Patients assigned to the two groups would preferably have overall reasonably matched characteristics such as age, gender, medical history, ethnic background, education level, severity of their Alzheimer's disease, etc.

B. IVIG Administration

As routinely practiced in the modern medicine, sterilized preparations of concentrated immunoglobulins (especially IgGs) are used for treating medical conditions that fall into these three main classes: immune deficiencies, inflammatory and autoimmune diseases, and acute infections. One commonly used IgG product, intravenous immunoglobulin or IVIG, is formulated for intravenous administration. Although concentrated immunoglobulins may also be formulated for subcutaneous administration, for ease of discussion, such subcutaneously formulated IgG compositions are also included in the term "IVIG" in this application. IVIG products suitable for use in practicing this invention may be obtained from a number of commercial suppliers, including Baxter BioScience, Talecris Biotherapeutics, Grifols USA, Octapharma USA, and ZLB Behring.

To successfully treat a disease or condition, a therapeutic agent must be administered in an effective amount. The term "effective amount" refers to an amount of a therapeutic agent, such as an IVIG preparation, that results in a detectable improvement or remediation of a medical condition being treated in the subject (e.g., Alzheimer's disease). An effective amount to be administered to the subject can be determined by a physician with consideration of individual differences in age, weight, disease severity, dose and frequency of administration, and individual response to the therapy. In certain embodiments, an IVIG product can be administered to a subject within the range of about 0.2 g/kilogram of patient body weight to about 4 g/kilogram body weight each time, and the frequency of administration may range from twice a week, once a week, twice a month, once a month, or once every other month. One exemplar dose range of IVIG is between about 0.1 to about 1 or about 0.2 to about 0.8 g/kg patient body weight, typically administered at the frequency of twice a month or once a month. For instance, IVIG is administered to some Alzheimer's patients at the dose of 0.2, 0.4, or 0.8 g/kg body weight according to a twice-a-month schedule. In other cases, IVIG is administered at the dose of 0.2, 0.4, or 0.8 g/kg body weight according to a once-a-month schedule.

The duration of IVIG treatment for Alzheimer's disease can vary: it may be as short as 3 or 6 months, or may be as long as 18 months, 2 years, 5 years, or 10 year. In some case, the IVIG treatment may last the remainder of a patient's natural life. Effectiveness of the IVIG treatment may be assess during the entire course of administration after a certain time period, e.g., every 3 months or every 6 months for an 18-month treatment plan. In other cases, effectiveness may be assessed every 9 or 12 months for a longer treatment course. The administration schedule (dose and frequency) may be adjusted accordingly for any subsequent administration. This scheme of assessment and adjustment need not be limited to the IVIG treatment of Alzheimer's disease: any other therapeutic brain preserving agent used or proposed for Alzheimer's disease treatment may be analyzed and followed in the same or similar manner.

III. Monitoring Ventricular Volume and Assessing Therapeutic Efficacy

A number of brain disorders exhibit enlarged ventricular space. Often such enlargement, especially in Alzheimer's disease, is believed to correlate with brain atrophy and therefore further deterioration of the brain condition. The present inventors discovered that ventricular enlargement rate correlates closely with response to IVIG treatment, and that therapeutic intervention with a brain preserving therapy shows decreased, measurable ventricular enlargement or brain atrophy which correlates to improvement in cognitive function as indicated by neuropsychological evaluation. As the commonly used methods for assessing a person's cognitive ability are time-consuming to administered and rely on the administrator's subjective judgment in the analysis, changes in ventricular volume can be readily detected and quantified by imaging methods. Monitoring ventricular enlargement rate therefore provides a far more objective and reliable standard for assessing the response to IVIG treatment.

A variety of methods are known to the medical professionals for imaging the brain for visualizing and quantifying ventricular volume. CT scan and MRI are among the most frequently used. Software for showing the images and analyzing changes in ventricular space is typically provided with the imaging equipment from the manufactures but may also be obtained according to specific needs from commercial suppliers.

For the purpose of analyzing the effects of a therapeutic modality such as IVIG on Alzheimer's patients receiving the therapy and determining any modification of future treatment plan, ventricular volume is monitored on a pre-determined time schedule. For example, patients on IVIG treatment may be imaged every 3 months or every 6 months for the duration of their treatment, with the first time point being just prior to the start of the treatment. Their ventricular volume is determined for each time point and comparisons are made for each ventricular volume starting from the second time point with the ventricular volume at the previous time point to determine a change. This change is then compared against an "expected" rate of ventricular enlargement in an Alzheimer's patient of similar state but without any anti-Alzheimer brain preserving treatment. If the observed change is smaller than the "expected" rate of enlargement, treatment for the time period between the two time points is deemed effective. If the observed change is equal to or greater than the "expected" rate of enlargement, treatment for the time period between the two time points is deemed ineffective. Various actions may then be taken depending on the specific circumstances. For example, if the treatment is deemed ineffective after relatively low dose or low administration frequency has been used, the physician may consider increasing the dose or administration frequency for the patient and observe for the next time period for signs of improved effectiveness. On the other hand, if the treatment is deemed ineffective after the therapeutic modality has already been given at a very high dose and/or administration frequency, especially after at least one round of treatment and efficacy determination steps, the physician may find the treatment ineffective for the particular patient and order the treatment discontinued. Similarly, when the therapy is deemed effective, the physician may also have the option to either maintain the same schedule of treatment or, as appropriate in some cases, modify slightly the treatment plan for further assessment and adjustment as needed.

For the purpose of assessing the effectiveness of a therapeutic agent intended or proposed for treating Alzheimer's disease by preserving a patient's brain (as opposed to merely alleviating symptoms), ventricular volume change in patients having Alzheimer's disease is compared between the therapeutic group (i.e., the group that has received the therapeutic agent) and non-therapeutic group (i.e., the group that has not received the therapeutic agent). Briefly, the average rate of ventricular enlargement in the non-therapeutic group is determined over a time period and then compared with the average rate of ventricular enlargement in the therapeutic group is determined over a time period. If the therapeutic group has an average ventricular enlargement rate lower than that of the non-therapeutic group, the therapeutic agent is deemed effective for preserving brain volume and function. Otherwise, the therapy is deemed ineffective for preserving brain volume and function. Although not required, the time periods during which the therapeutic group and non-therapeutic group ventricular enlargement rates are determined are typically of the same length and run concurrently. To ensure the comparison and assessment is accurate, each of the therapeutic and non-therapeutic group should include a reasonable number of individuals, for example, at least 5, 8, or 10, or at least 12, 15, or 20 people.

EXAMPLES

The following examples are provided by way of illustration only and not by way of limitation. Those of skill in the art will readily recognize a variety of non-critical parameters that could be changed or modified to yield essentially the same or similar results.

Example I

Neuropsychological Outcomes Following 18 Months of Uninterrupted Intravenous Immunoglobulin (IVIG) Treatment in Patients with Alzheimer's Disease IVIG Phase 2 Study Design: The study was a randomized, double-blind, placebo-controlled, parallel arm, add-on clinical trial testing safety and utility/futility of IVIG treatment for Alzheimer's Disease (AD). 24 subjects with mild to moderate AD (as determined by MMSE 14-26) participated in the trial. For the placebo group, a 6-month placebo period was controlled with a 12-month open-label extension. Primary clinical outcomes were measured by ADAS-Cog and CGIC, where a positive outcome was predefined as a difference of at least 1.7 ADAS-Cog points at 6 months in IGIV group and numeric superiority on CGIC. Secondary clinical outcomes were measured by NPI, ADCS-ADL, QOL, 3MS, and neuropsychological battery. FIG. 1 provides an outline of the study design.

Dosage range: IVIG infusion was given at the frequency of once per 2 weeks or once per 4 weeks at the single dose of 0.2, 0.4, or 0.8 grams IVIG per kg patient body weight.

Patient demographics and baseline performance: Provided in Tables 1 and 2.

TABLE 1

Baseline Demographics

|  | Placebo (P)<br>n = 8 | IVIG (all)<br>n = 16 | stats test |
|---|---|---|---|
| Age, years | 72.3 (SD 8.2) | 71.1 (SD 9.6) | NS |
| Gender | 5 F/3 M | 7 F/9 M | — |
| Ethnicity | 7 white/1 other | 15 white/1 other | — |
| Education, years | 14.1 (SD 3.6) | 16.1 (SD 2.5) | NS |
| Years since Diagnosis | 1.78 (SD 1.61) | 1.82 (SD 1.70) | NS |
| AChE Inhibitors | 100% | 100% | NS |
| Namenda | 75% | 81.25% | NS |
| APOE E4 Carriers | 50%<br>(n = 8) | 79%<br>(n = 14) | — |

TABLE 2

Baseline Performance

|  | Placebo (P)<br>Mean (SD) | IVIG (all)<br>Mean (SD) | stats test |
|---|---|---|---|
| Primary Measure | | | |
| ADAS-Cog | 25.17 (4.24) | 22.44 (7.47) | NS |
| Secondary Measures | | | |
| ADLs | 65.25 (12.30) | 70.40 (5.99) | NS |
| GDS | 4.80 (3.11) | 4.87 (4.34) | NS |
| NPI | 5.00 (5.29) | 4.87 (8.94) | NS |
| QOL caregiver | 36.25 (3.58) | 36.27 (5.95) | NS |

TABLE 2-continued

Baseline Performance

|  | Placebo (P) Mean (SD) | IVIG (all) Mean (SD) | stats test |
|---|---|---|---|
| QOL patient | 41.17 (3.06) | 42.27 (5.42) | NS |
| 3MS | 62.33 (6.62) | 70.93 (14.50) | NS |

ADAS-Cog: Alzheimer's Disease Assessment Scale-Cognitive Subscale;
ADLs: Activities of Daily Living;
GDS: Geriatric Depression Scale;
NPI: Neuropsychiatric Inventory;
QOL: Quality of Life;
3MS: Modified Mini Mental Status Examination.
*There were no significant differences between arms in these measures at baseline.

Figure 2:
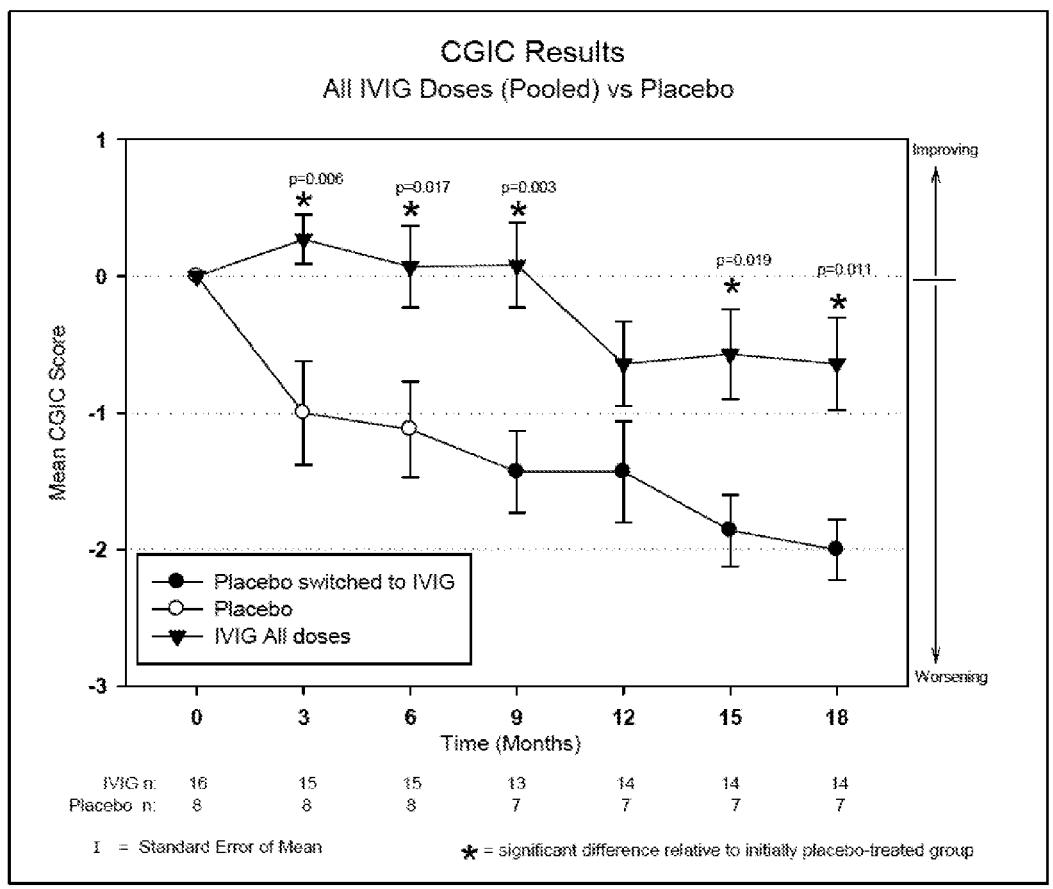
FIG. 2 compares the IVIG group and the placebo group in CGIC scores during the 18-month study.
Figure 3:
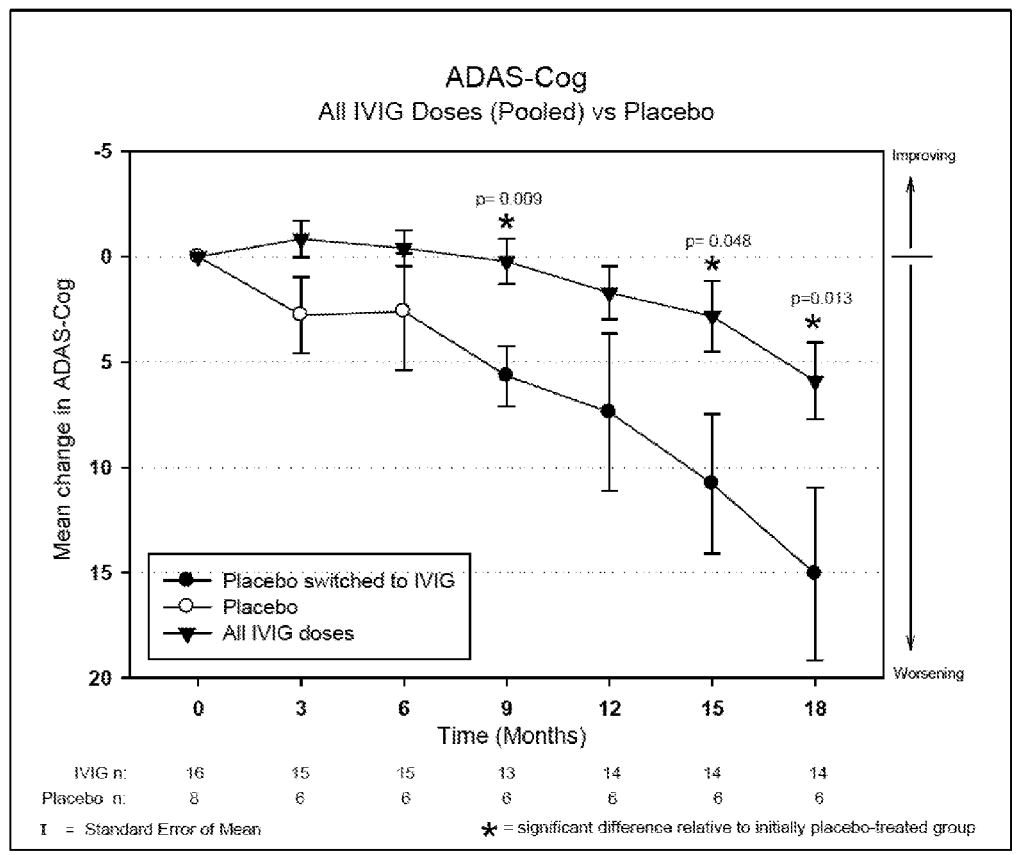
FIG. 3 compares the IVIG group and the placebo group in ADAS-Cog scores during the 18-month study.
Figure 4A:
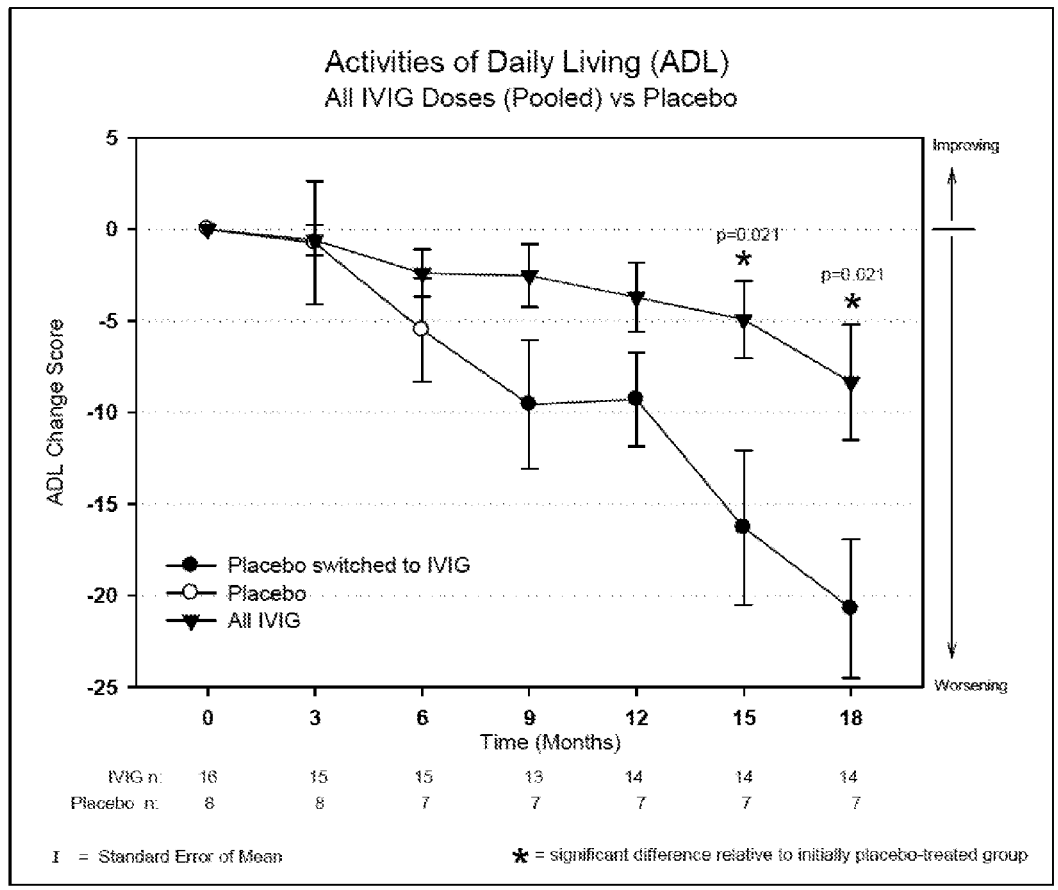
FIGS. 4A-4D compare the IVIG group and the placebo group in Activities of Daily Living (ADL), Neuropsychiatric Inventory (NPI), Quality of Life (QOL) Inventory (Caregiver), and Modified Minimental (3MS) tests, respectively, during the 18-month study.
Figure 4B:
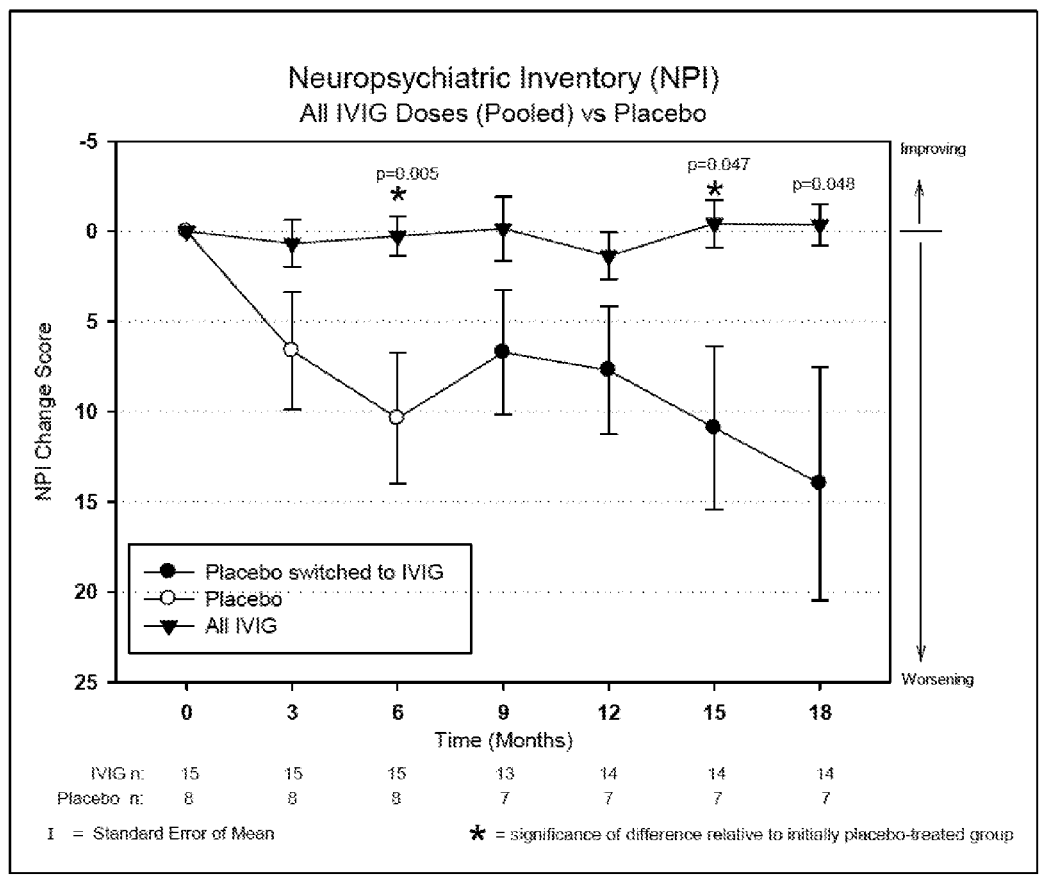
Figure 4C:
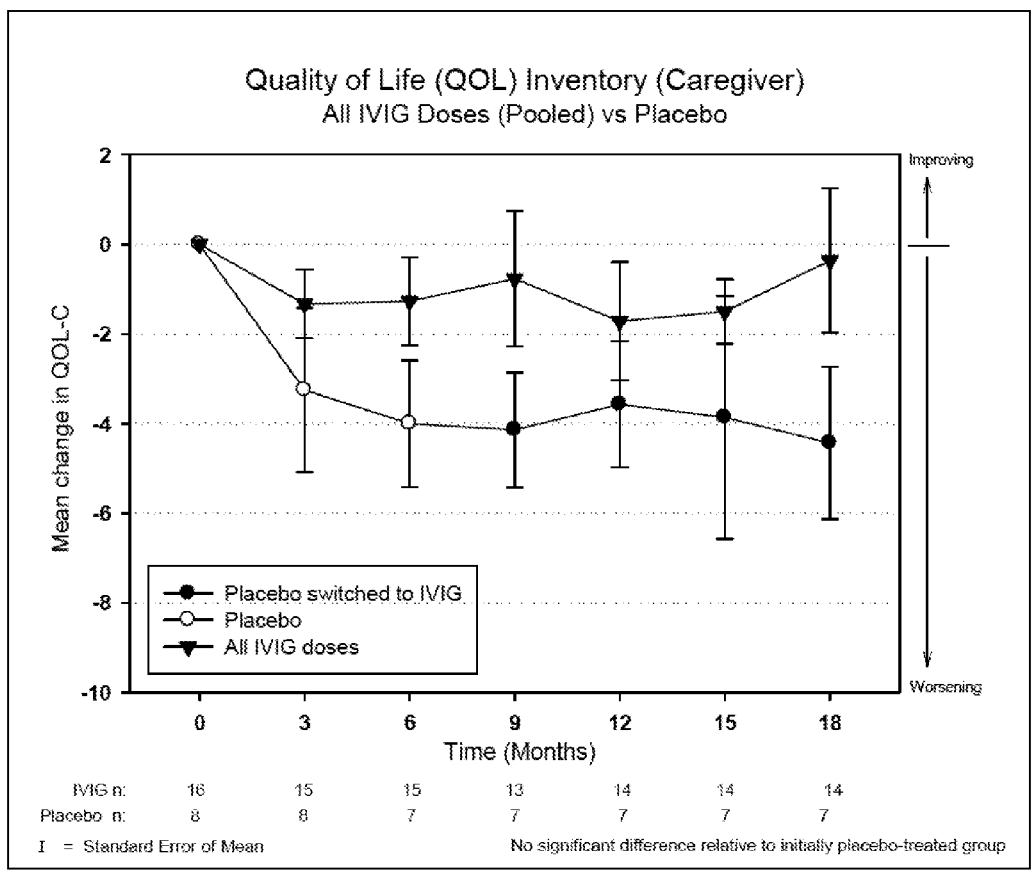
Figure 4D:
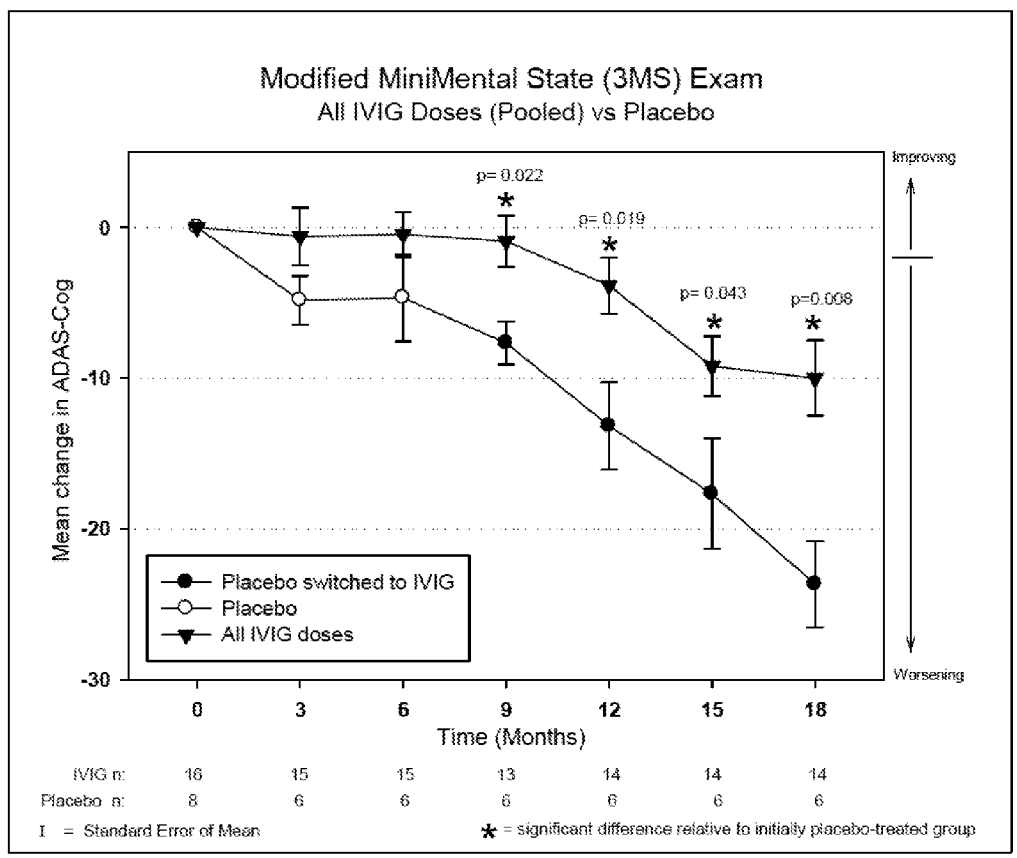

Results: improvement in CGIC scores (FIG. 2) and ADAS-Cog (FIG. 3) was observed when the IVIG group (all doses pooled) was compared with the placebo group (switched to IVIG after the initial 6 months). Similarly, improvement was also observed in various secondary measures when the IVIG group was compared with the placebo group (FIGS. 4A-4D).

Figure 5:
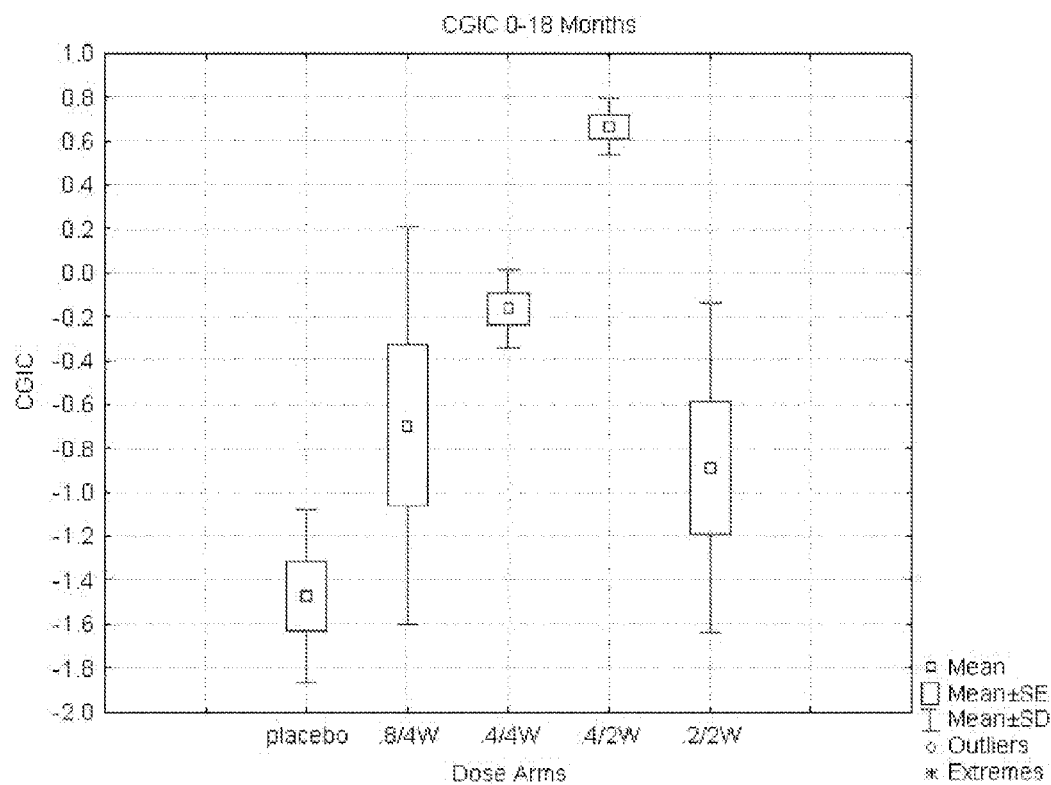
FIG. 5 shows the mean baseline change in CGIC scores from 0 to 18 months of the placebo group and four IVIG groups (0.8 g/kg/4 wk; 0.4 g/kg/4 wk; 0.4 g/kg/2 wk; 0.2 g/gk/2 wk).
Figure 6:
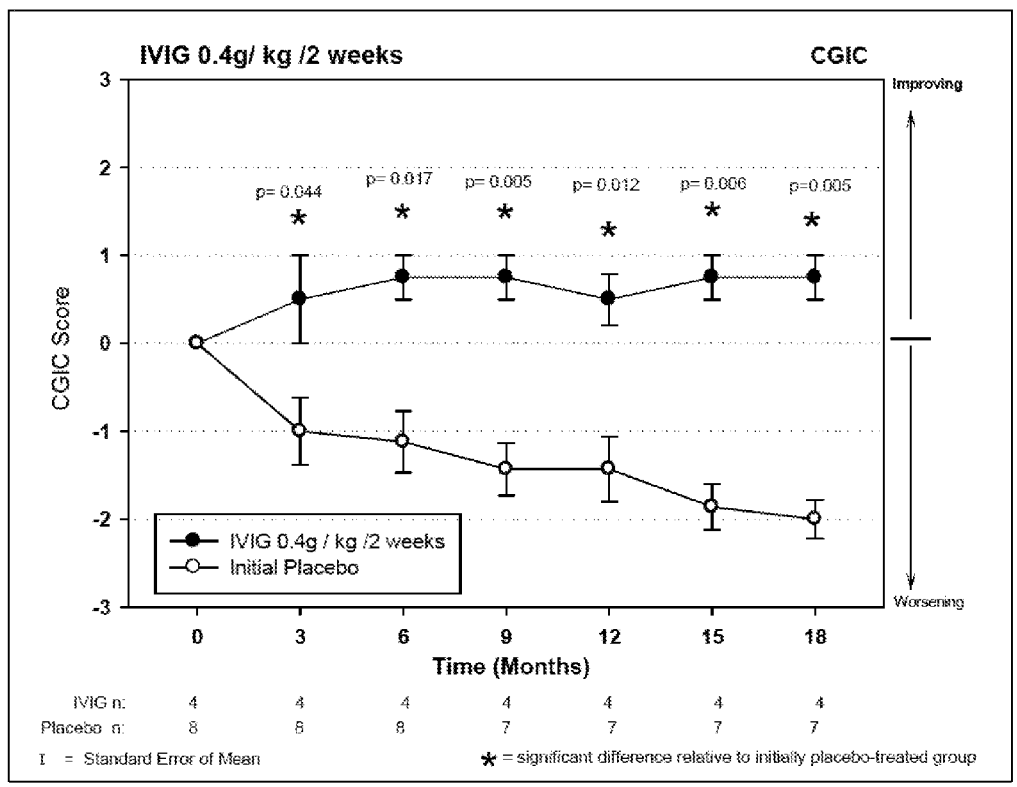
FIG. 6 compares the placebo group and the IVIG 0.4 g/kg/2 wk group in CGIC scores from 0 to 18 months.

The effects of IVIG treatment at different dosing schedules are shown in FIG. 5, where mean change in CGIC scores from baseline to 18 months are compared among the placebo group and 4 IVIG groups (0.8 g/kg once per 4 weeks; 0.4 g/kg once per 4 weeks; 0.4 g/kg once per 2 weeks; and 0.2 g/kg once per 2 weeks). The group that received 0.4 g/kg infusion every 2 weeks demonstrates the most notable improvement from the baseline CGIC score. When the 0.4 g/kg/2 wk group is compared with the placebo group over the course of 18 months, improvement of statistical significance is observed at all time points (FIG. 6).

Figure 7:
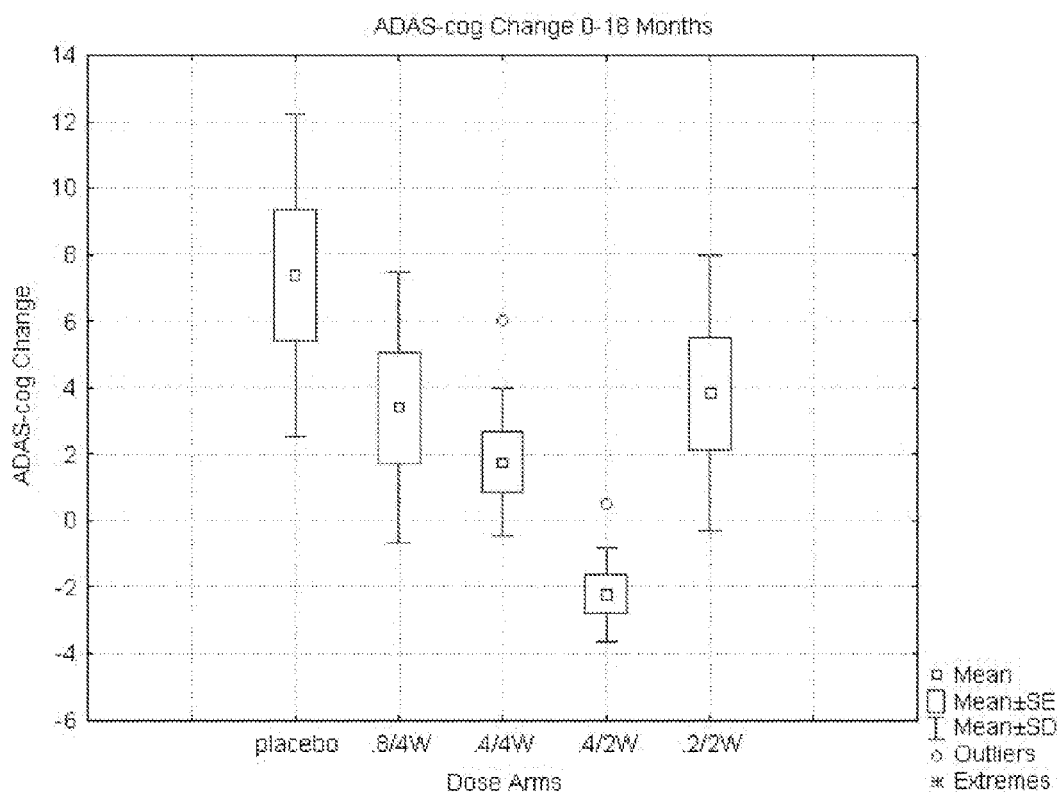
FIG. 7 shows the mean baseline change in ADAS-Cog scores from 0 to 18 months of the placebo group and four IVIG groups (0.8 g/kg/4 wk; 0.4 g/kg/4 wk; 0.4 g/kg/2 wk; 0.2 g/gk/2 wk).
Figure 8:
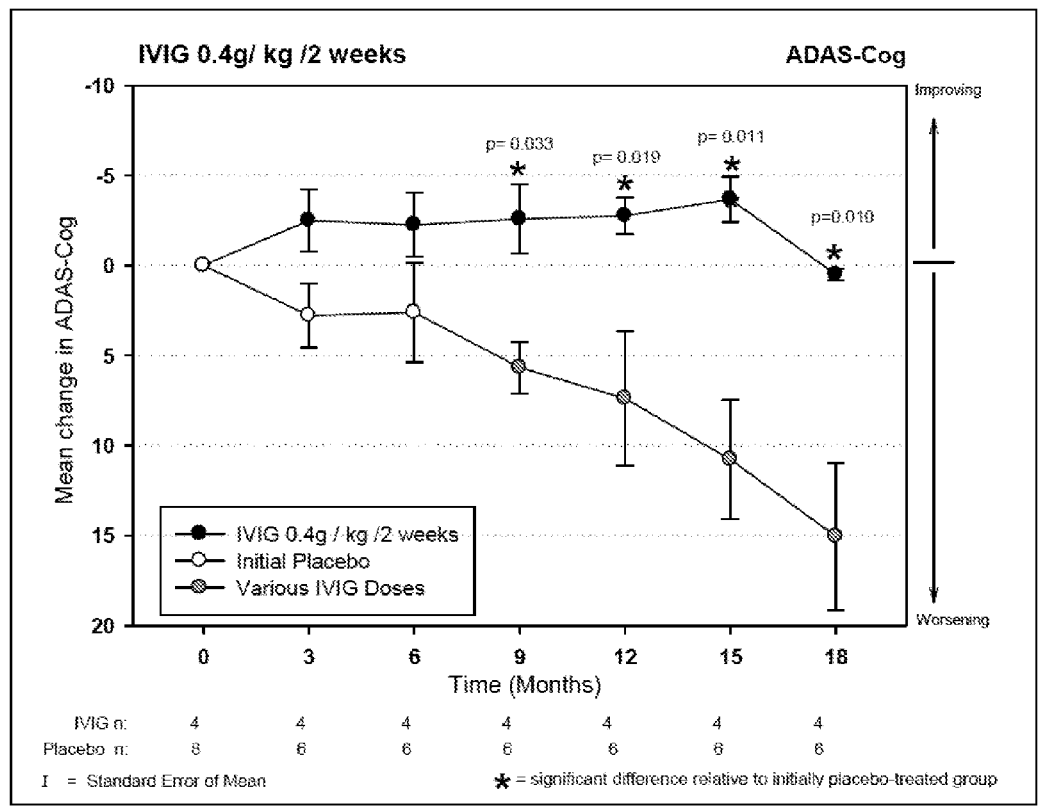
FIG. 8 compares the placebo group and the IVIG 0.4 g/kg/2 wk group in ADAS-Cog scores from 0 to 18 months.
Figure 9:
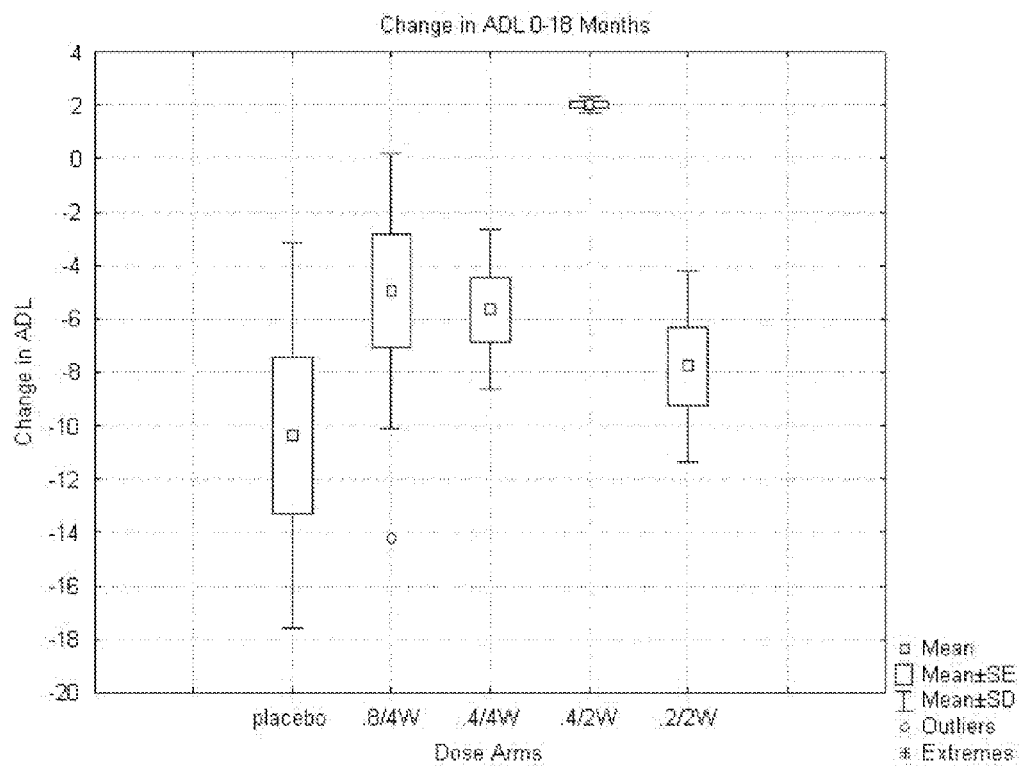
FIG. 9 shows the mean baseline change in ADL test scores from 0 to 18 months of the placebo group and four IVIG groups (0.8 g/kg/4 wk; 0.4 g/kg/4 wk; 0.4 g/kg/2 wk; 0.2 g/gk/2 wk).
Figure 10:
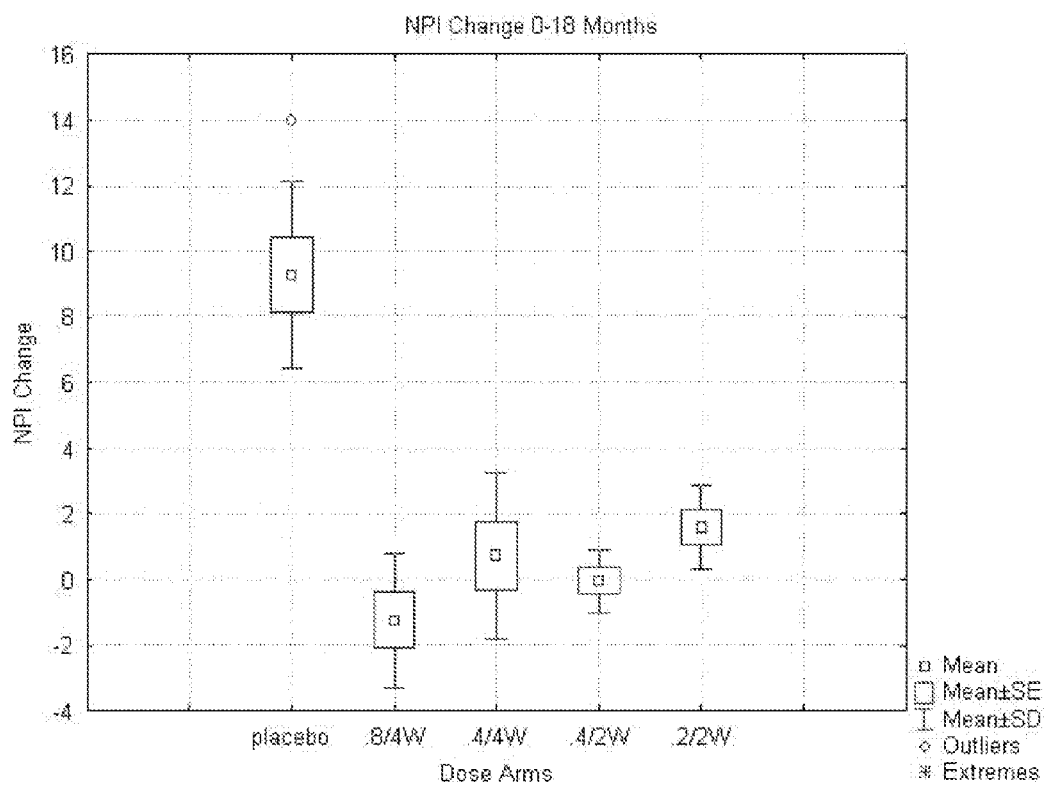
FIG. 10 shows the mean baseline change in NPI test scores from 0 to 18 months of the placebo group and four IVIG groups (0.8 g/kg/4 wk; 0.4 g/kg/4 wk; 0.4 g/kg/2 wk; 0.2 g/gk/2wk).
Figure 11:
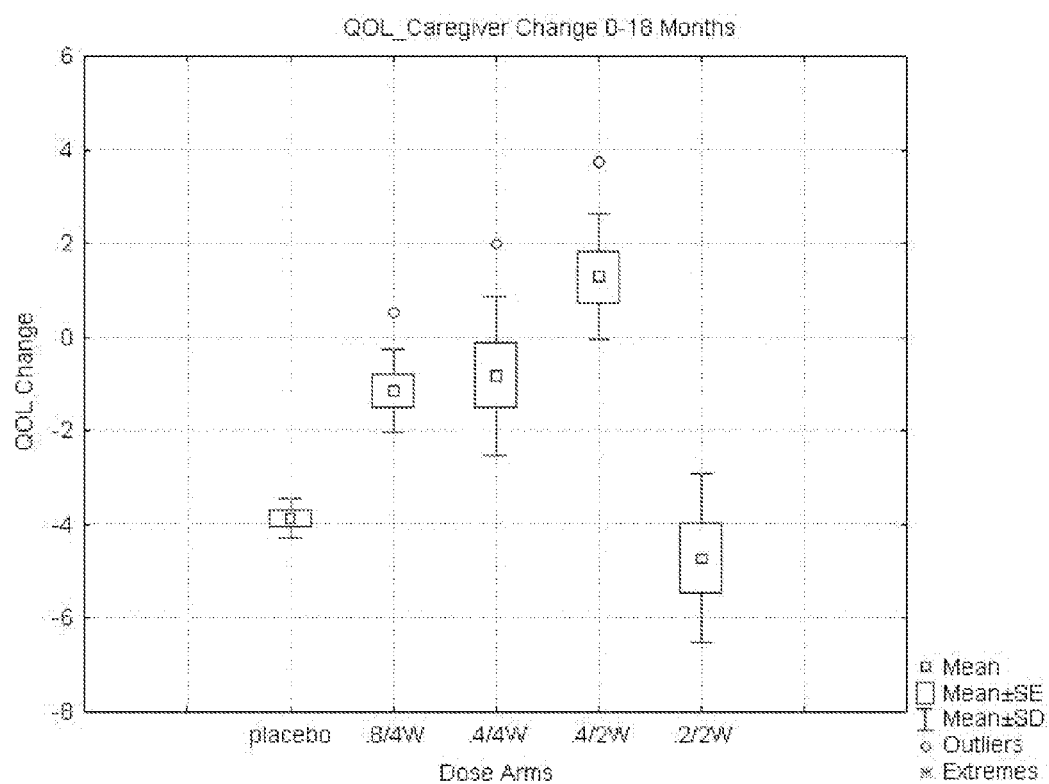
FIG. 11 shows the mean baseline change in QOL-Caregiver test scores from 0 to 18 months of the placebo group and four IVIG groups (0.8 g/kg/4 wk; 0.4 g/kg/4 wk; 0.4 g/kg/2 wk; 0.2 g/gk/2 wk).
Figure 12:
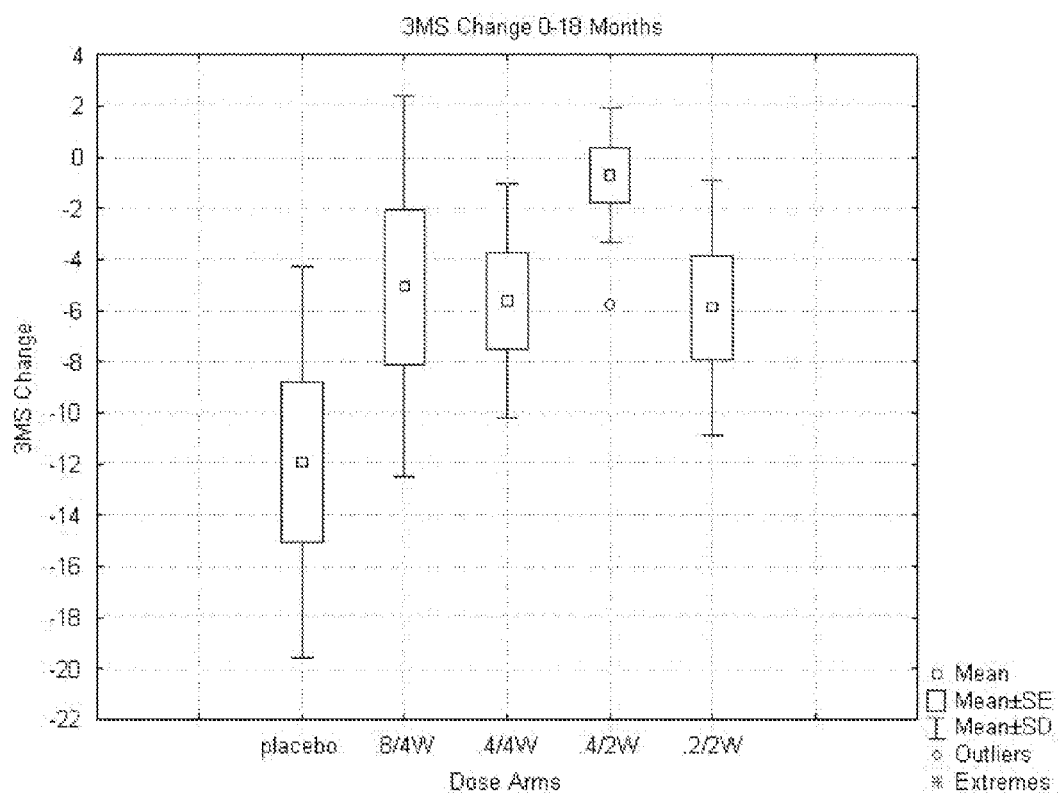
FIG. 12 shows the mean baseline change in 3MS test scores from 0 to 18 months of the placebo group and four IVIG groups (0.8 g/kg/4 wk; 0.4 g/kg/4 wk; 0.4 g/kg/2 wk; 0.2 g/gk/2 wk).

FIG. 7 shows the effect of IVIG treatment on ADAS-Cog scores from baseline to 18 months by comparing the placebo group with 4 IVIG groups (0.8 g/kg once per 4 weeks; 0.4 g/kg once per 4 weeks; 0.4 g/kg once per 2 weeks; and 0.2 g/kg once per 2 weeks). The group that received 0.4 g/kg infusion every 2 weeks again shows the most notable improvement from the baseline ADAS-Cog results.

FIGS. 9-12 show the effect of IVIG treatment on secondary measures of ADLs, and 3MS, respectively, by comparing the placebo group with 4 IVIG groups (0.8 g/kg once per 4 weeks; 0.4 g/kg once per 4 weeks; 0.4 g/kg once per 2 weeks; and 0.2 g/kg once per 2 weeks). The 0.4 g/kg/2 wk group consistently achieved the most improvement.

Table 3 provides a responder analysis at 18 months of the study.

TABLE 3

18 Months Responder Analysis (Criteria for response = CGIC score ≥ −1 at 18 months)

| Domain | Task | Mean Change |
|---|---|---|
| Attention | WAIS-III Digit Span Forward (p = 0.022) | R: −0.08 NR: −1.43 |
| Working Memory | WAIS-III Digit Span Backward (p = 0.002) | R: −0.38 NR: −1.86 |
|  | ADAS-Cog: Remembering Test Instructions (p = 0.004) | R: 0.23 NR: 2.71 |
| Conceptualization | Clock Draw (p = 0.005) | R: 0.50 NR: −2.57 |
| Verbal Fluency | COWAT FAS (p = 0.054) | R: −3.00 NR: −13.50 |
| Language | ADAS-Cog Spoken Language Ability (p = 0.002) | R: 0.15 NR: 1.57 |
|  | ADAS-Cog Comprehension (p = 0.040) | R: 0.00 NR: 1.43 |
| Construction | Clock Copy (p = 0.026) | R: 0.25 NR: −0.86 |

100% of subjects with CGIC scores of 0 or 1 at 6 months were Responders at 18 months
0% of subjects with CGIC scores less than 0 at 6 months were Responders at 18 months Safety and Tolerability: 21 of 24 subjects completed the 18-month treatment (12.5% attrition). 632 out of 648 planned infusions were successfully administered (98.25% compliance). There were no serious treatment-related adverse events: although one SAE occurred (new onset seizure disorder), it was deemed not to be treatment-related. AEs that occurred at a greater than expected frequency in subjects receiving IVIG included non-hemolytic anemia (20.8%) and rash (20.8%). IVIG was generally safe and well-tolerated by AD patients in this study.

Conclusion: Uninterrupted IVIG treatment of AD patients for 18 months resulted in significantly better outcomes on the CGIC, ADAS-Cog, ADL and NPI scales compared to initial placebo treatment. Subjects who responded to IVIG at 18 months performed significantly better than non-responders in language functioning and construction and on tests of executive function, including attention, working memory, conceptualization, and verbal fluency tasks. Significant dose dependency was observed favoring the IVIG 0.4 g/kg/2 W dose arm. IVIG was safe and well-tolerated by the AD patients in this study. The results of this 18-month study were strongly correlated with rates of brain atrophy measured by serial MRIs.

Example II

Intravenous Immunoglobulin Treatment Decreases Rates of Ventricular Enlargement and Cognitive Decline in Alzheimer's Disease Objectives: To examine the effect of 18 months of intravenous Immunoglobulin (IVIG) treatment on ventricular enlargement rates in mild to moderate Alzheimer's disease (AD); to examine the correlation between ventricular enlargement rates and clinical outcomes in AD patients treated with IVIG.

Neuronal loss during normal aging causes brain atrophy (or shrinkage). Neuronal degeneration in Alzheimer's Disease, however, causes accelerated brain atrophy. As the human skull is a closed space, brain atrophy leads to progressive enlargement of the fluid-filled cerebral ventricles. The rate of ventricular enlargement over time provides an objective measure of the rate of Alzheimer's disease progression.

Different ventricular enlargement rates have been observed in normal, mild cognitive impairment (MCI), and Alzheimer's disease brains. It has been reported in the literature, for instance, normal elderly people have about 3-6% (others indicate the range of 1.5-3%) in annual ventricular volume change and about 0.5-1% (others indicate the range of less than 0.7%) annual brain volume change, in contrast to people with MCI having about 6-8% in annual ventricular volume change and about 1-2% annual brain volume change, and people with AD having about 8-12% (others indicate the range of 5-16%) in annual ventricular volume change and about 2-4% (others indicate the range of 1.4-2.2%) annual brain volume change.

Ventricular volume measurements have certain advantages over other brain volumetric analyses that could be used to monitor brain atrophy. One such advantage is that ventricular volume measurements have more favorable signal to noise characteristics. For instance, studies have indicated that volumetric measurement of hippocampus records an annual change of 5% in AD patients with an measurement error of 2-5%, and volumetric measurement of whole brain records an annual change of 2-4% in AD patients with an measurement error of 0.5-1%; whereas ventricular volume measurement can detect an annual change of 8-12% in AD patients with an measurement error of 0.5-1%.

Methods: All scans were performed on a 3T MRI scanner using 3D-SPGR sequences. Ventricular volume was quantified using Freesurfer and Brain Ventricular Quantification software. Ventricular enlargement rates (VERs) were calculated from the difference between baseline and 18 months ventricular volumes divided by the product of baseline volumes and interscan intervals. Image analysis was performed blinded to treatment assignments and clinical outcomes.

MRI brain images and clinical outcome data were collected over 18 months in the Phase 2 study of Gammagard IVIG (Baxter) for treatment of mild to moderate AD. Subjects completing a baseline volumetric MRI as well as one follow-up MRI after 18 months of study participation were included in this analysis. Ventricular volume changes are analyzed by comparing subjects treated continuously over 18 months with IVIG to those treated initially with placebo.

MRI measurements were performed on a 3T GE Echospeed MRI scanner. 128 serial slices of 1 mm thickness were obtained through the entire brain volume. An 3D-SPGR sequence was employed, which was sufficient for whole brain and ventricles volumetry but suboptimal for grey and white matter segmentation and detailed sub-region analyses. Post-processing of imaging data was performed blinded to study arm assignments and clinical outcomes. Automated quantification of ventricular volume was initially performed using FREESURFER, a brain volumetric software package. Ventricular volume measurements were verified using BRAIN VENTRICULAR QUANTIFICATION (BVQ) software. Longitudinal assessment of brain volume changes and measurement of total intracranial volume was performed using SIENA.

Results: 20 of 24 study participants had evaluable MRI data, including 6 initially assigned to placebo and 14 randomized to IVIG. Mean annual VER among all subjects assigned to IVIG was 7%, significantly less (p=0.048) than the 12% rate in the placebo group. VER was significantly correlated with CGIC (r=-0.58, p=0.006) and ADAS-Cog changes scores (r=0.64, p=0.007) at 18 months. VER varied with IVIG dose and was lowest (2.63%, p=0.048) in subjects receiving IVIG 0.4 g/kg bimonthly, the dose that produced the most favorable clinical outcomes.

Figure 13:
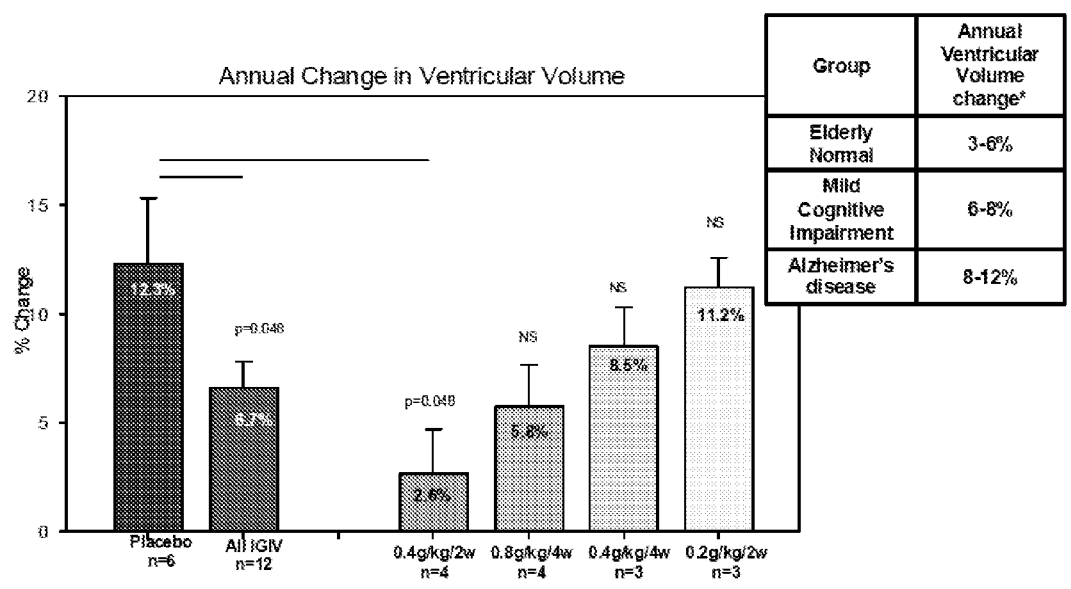
FIG. 13 shows annual change in ventricular volume during the 18-month study in the placebo group, four IVIG groups (0.8 g/kg/4 wk; 0.4 g/kg/4 wk; 0.4 g/kg/2 wk; 0.2 g/gk/2 wk), and all IVIG group.
Figure 14:
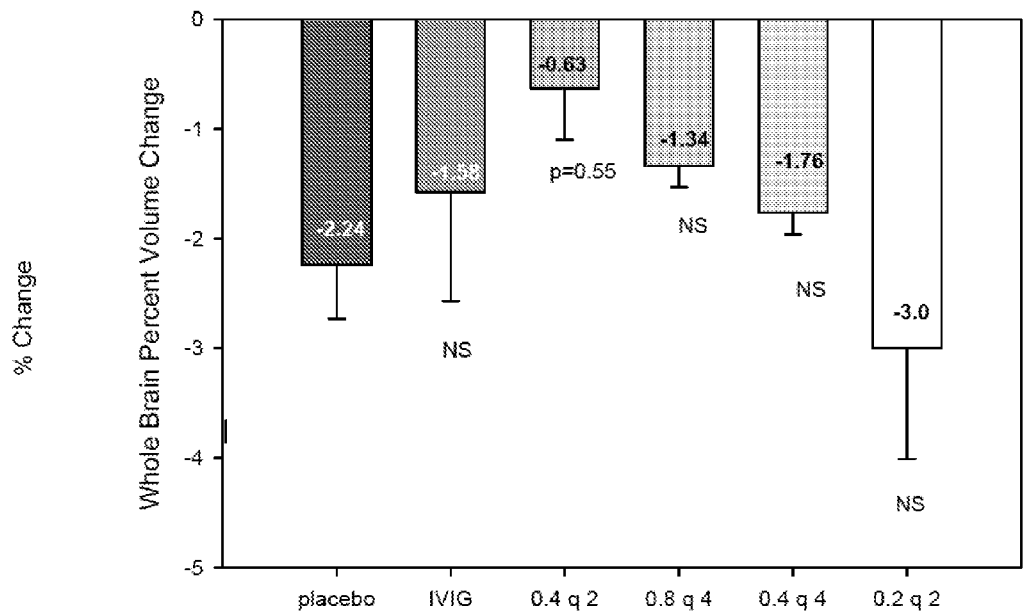
FIG. 14 shows the effects of IVIG treatment in the 18-month study by comparing whole brain percent volume change in the placebo group, four IVIG groups (0.8 g/kg/4 wk; 0.4 g/kg/4 wk; 0.4 g/kg/2 wk; 0.2 g/gk/2 wk), and all IVIG group.
Figure 15A:
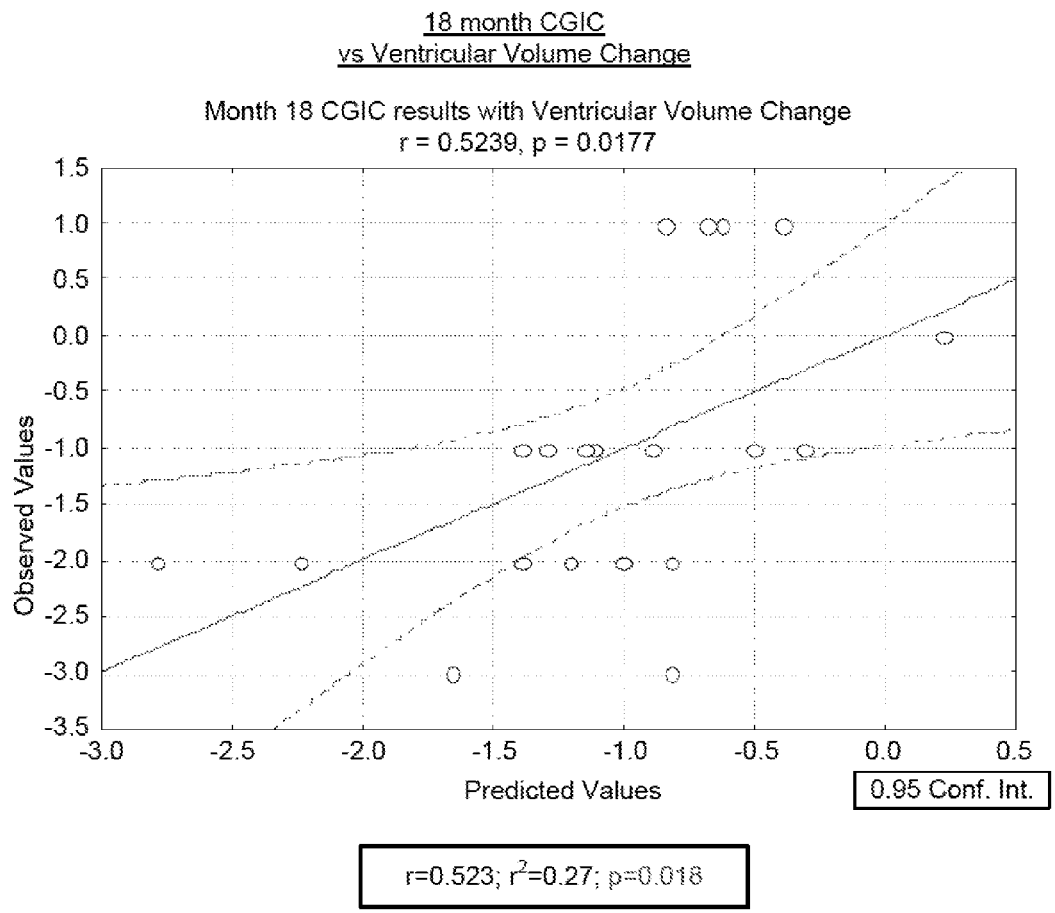
FIG. 15 shows the correlation between changes in ventricular volume and two cognitive test scores (CGIC and ADAS-Cog) in the 18-month study.
Figure 15B:
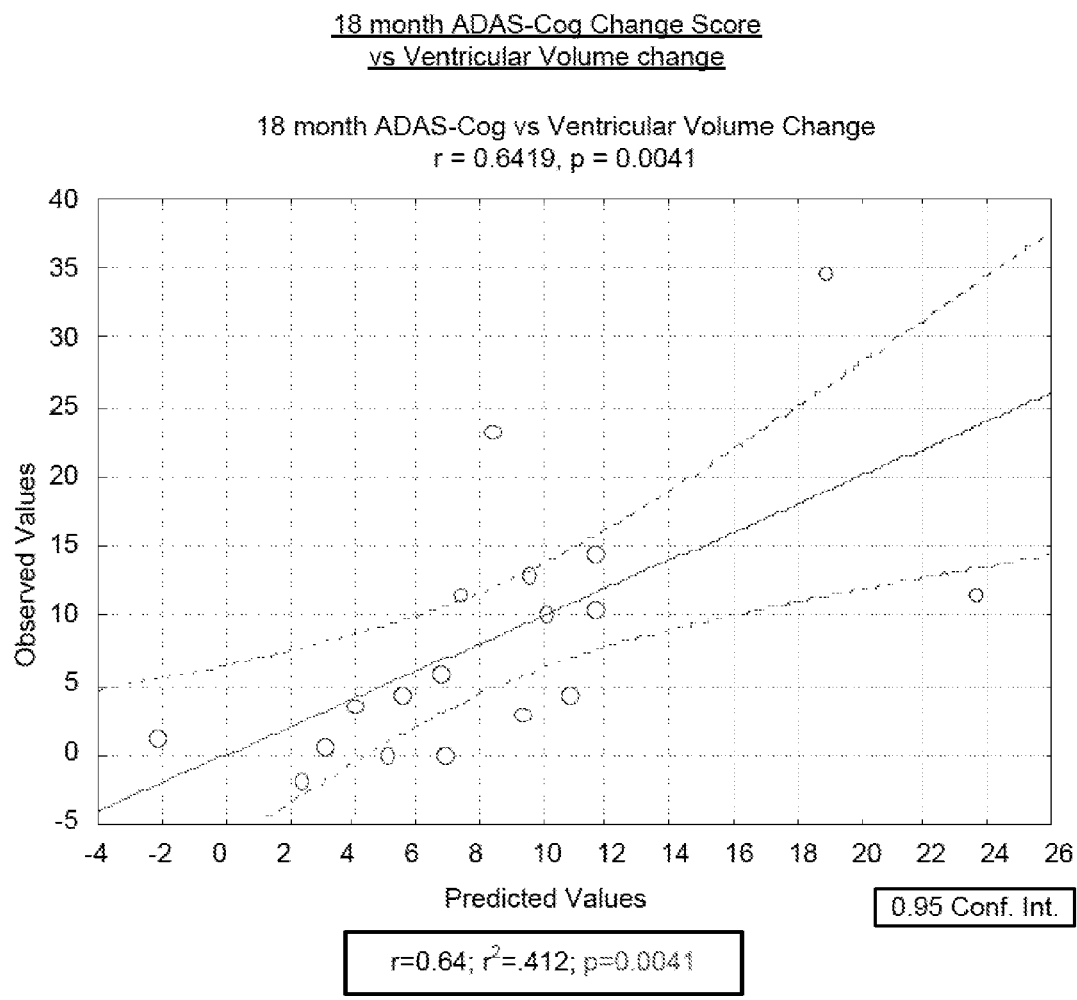
Figure 16A:
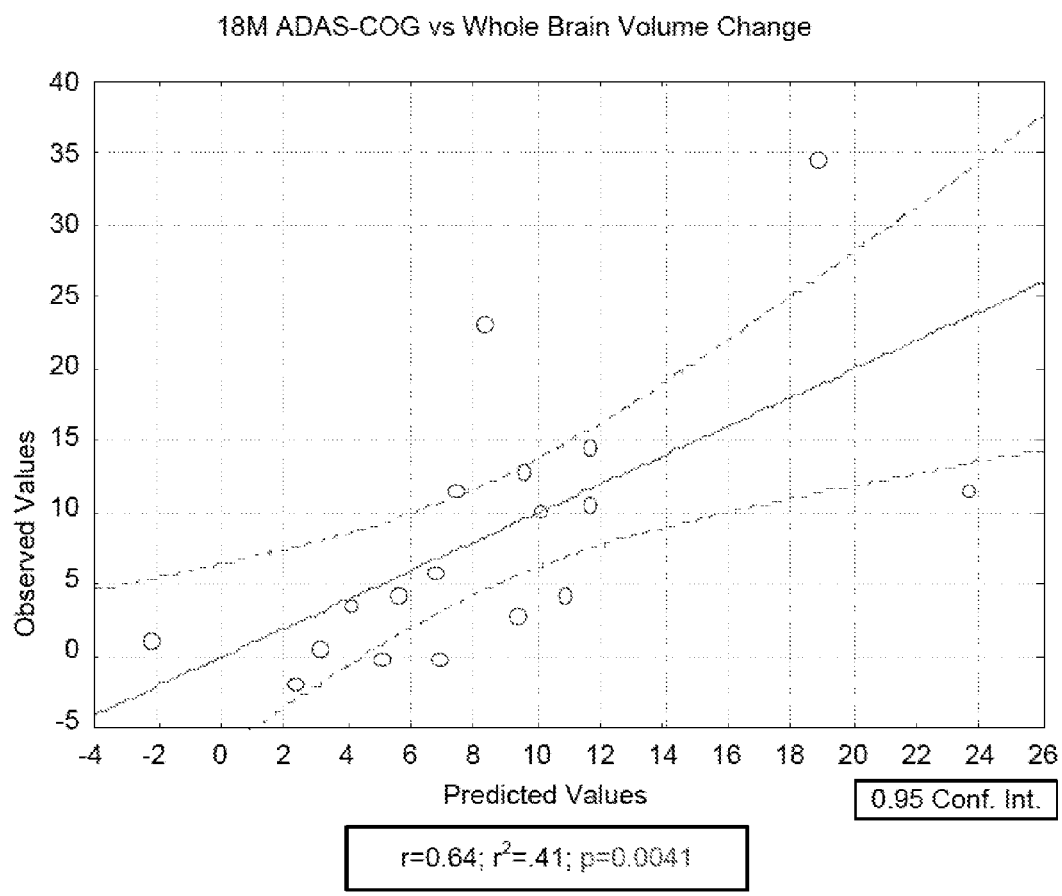
FIG. 16 shows the correlation between change in whole brain volume and two cognitive test scores (CGIC and ADAS-Cog) in the 18-month study.
Figure 16B:
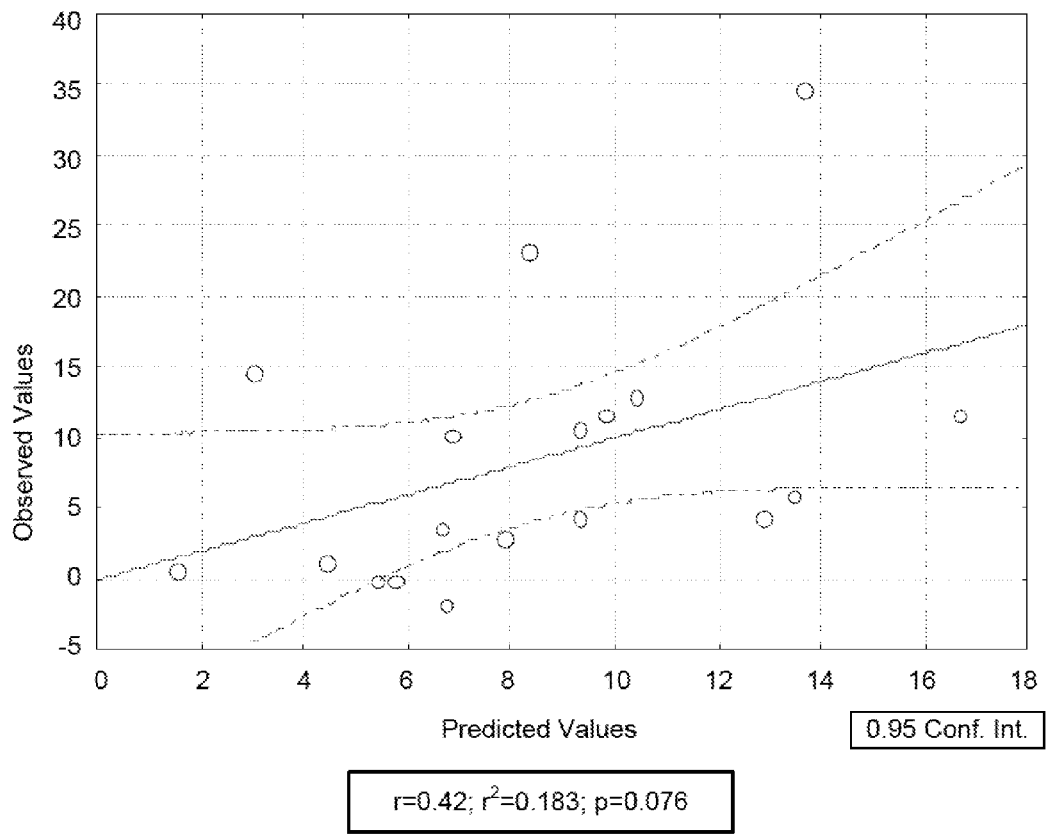

FIG. 13 compares annual change in ventricular volume among AD patients who received placebo or IVIG during the 18-month study, where IVIG treatment shows a significantly decreased VER. FIG. 14 compares changes in whole brain volume among AD patients who received placebo or IVIG during the 18-month study, where IVIG treatment again shows a significantly reduced rate of brain atrophy. FIG. 15 shows the correlation between changes in VER and two cognitive test scores (CGIC and ADAS-Cog) in the 18-month study. FIG. 16 shows the correlation between change in whole brain volume and two cognitive test scores (CGIC and ADAS-Cog) in the 18-month study.

Conclusion and Discussion: Volumetric MRI measurements indicated a significant reduction in rates of ventricular enlargement and brain atrophy in AD patients with 18 months of uninterrupted IVIG treatment. The effectiveness of IVIG treatment varied with IVIG dose and correlated with reduced cognitive decline. IVIG's effects on brain atrophy were highly correlated with clinical outcomes (ADAS-Cog, CGIC) at 18 months. These results indicate that IVIG therapy can effectively reduce the rate of brain atrophy and inhibit disease progression in AD patients. It is worth noting that brain volume changes and clinical outcomes in AD patients treated with 0.4 g/kg/2 w were comparable to normal.

It was also observed that Alzheimer's disease progresses at different rates that vary among individual patients. Rate of progression of AD, however, appears to correlate with rate of change in ventricular volume and whole brain volume. No correlation was established between baseline brain atrophy and change in ventricular volume during the 18-month study. Neither was correlation found between baseline brain or ventricular volume and the rate of ventricular volume changes at 18 months. Likewise, no correlation was found with baseline age, gender, estimated IQ or educational attainment. The volumetric results at 18 months are therefore more likely indication of an IVIG treatment effect rather than pre-existing differences in the rate of progression of disease among individual patients.

All patents, patent applications, and other publications, including GenBank Accession Numbers, cited in this application are incorporated by reference in the entirety for all purposes.

What is claimed is:

1. A method for treating Alzheimer's disease in a subject in need thereof, comprising the sequential steps of:
   (a) determining ventricular volume in the subject's brain by magnetic resonance imaging (MRI), thereby obtaining a baseline value of ventricular volume;
   (b) administering a brain preserving therapeutic agent to the subject for the purpose of treating Alzheimer's disease during a first time period;
   (c) determining ventricular volume in the subject's brain by MRI, thereby obtaining a first intermediate value of ventricular volume;
   (d) comparing the intermediate value from step (c) with the baseline value from step (a); and
   (e) increasing administration of the brain preserving therapeutic agent in dose or frequency if step (d) indicates an increase from the baseline value to the first intermediate value and the increase is equal to or greater than an expected increase in ventricular volume in a subject with Alzheimer's disease within a time period of the same duration as the first time period but without receiving treatment for the disease, and
   maintaining administration of the brain preserving therapeutic agent in dose or frequency if step (d) indicates no increase from the baseline value to the first intermediate value or indicates an increase that is less than an expected increase in ventricular volume in a subject with Alzheimer's disease within a time period of the same duration as the first time period but without receiving treatment for the disease.

2. The method of claim 1, wherein steps (b) to (d) are further repeated at least once and in each repeat the latest intermediate value is compared with the second latest intermediate value to determine future administration of the therapeutic agent in the same manner as step (e).

3. The method of claim 2, wherein step (d) during any repeat indicates an increase from one intermediate value to its subsequent intermediate value and the increase is equal to or greater than an expected increase in ventricular volume in a subject with Alzheimer's disease within a time period of the same duration as the time period between the two intermediate values but without receiving treatment for the disease, and the administration of the brain preserving therapeutic agent is increased in dose or frequency, further comprising the steps of:

(f) determining ventricular volume in the subject's brain by MRI after an additional time period during which the therapeutic agent is administered to the subject, thereby obtaining additional intermediate value of ventricular volume;

(g) comparing the additional intermediate value with its previous intermediate value; and (h) discontinuing further administration of the therapeutic agent if step (g) indicates an increase from the previous intermediate value to the additional intermediate value and the increase is equal to or greater than an expected increase in ventricular volume in a subject with Alzheimer's disease within a time period of the same duration as the additional time period but without receiving treatment for the disease, and maintaining administration of the brain preserving therapeutic agent in dose or frequency if step (g) indicates no increase from the previous intermediate value to the additional intermediate value or indicates an increase that is less than an expected increase in ventricular volume in a subject with Alzheimer's disease within a time period of the same duration as the additional time period but without receiving treatment for the disease.

4. The method of claim 1, wherein the first time period is 3 months, 6 months, 9 months, 12 months, or 18 months.

5. The method of claim 2, wherein the second or subsequent time period is 3 months, 6 months, 9 months, 12 months, or 18 months.

6. The method of claim 1, wherein the therapeutic agent is an immunoglobulin-based brain preserving therapeutic agent.

7. A method for assessing efficacy of administration of intravenous immunoglobulin (IVIG) intended for treating Alzheimer's disease, comprising the steps of:

(a) performing magnetic resonance imaging (MRI) to determine the rate of change in ventricular volume of subjects suffering from Alzheimer's disease but not receiving IVIG, thereby obtaining an average rate of change in ventricular volume as a non-therapeutic rate of ventricular volume change;

(b) performing MRI to determine the rate of change in ventricular volume of subjects suffering from Alzheimer's disease and receiving IVIG, thereby obtaining an average rate of change in ventricular volume as a therapeutic rate of ventricular volume change; and (c) comparing the therapeutic rate with the non-therapeutic rate, thereby determining the efficacy of the administration of the brain preserving therapeutic agent, wherein the administration of IVIG is deemed effective if the therapeutic rate is lower than the non-therapeutic rate, and the administration of IVIG is deemed ineffective if the therapeutic rate is equal to or greater than the non-therapeutic rate.

8. The method of claim 7, wherein the rate of change in ventricular volume in step (a) or (b) is determined over a time period of about 3 months, 6 months, 9 months, 12 months, or 18 months.

9. The method of claim 3, wherein the second or subsequent time period is 3 months, 6 months, 9 months, 12 months, or 18 months.

* * * * *